US010223634B2

(12) United States Patent
Sussillo et al.

(10) Patent No.: US 10,223,634 B2
(45) Date of Patent: Mar. 5, 2019

(54) MULTIPLICATIVE RECURRENT NEURAL NETWORK FOR FAST AND ROBUST INTRACORTICAL BRAIN MACHINE INTERFACE DECODERS

(71) Applicant: The Board of Trustees of the Leland Stanford Junior University, Palo Alto, CA (US)

(72) Inventors: David Sussillo, Portola Valley, CA (US); Jonathan C. Kao, Stanford, CA (US); Sergey Stavisky, San Francisco, CA (US); Krishna V. Shenoy, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 704 days.

(21) Appl. No.: 14/826,300

(22) Filed: Aug. 14, 2015

(65) Prior Publication Data

US 2016/0048753 A1    Feb. 18, 2016

Related U.S. Application Data (60) Provisional application No. 62/037,441, filed on Aug. 14, 2014.

(51) Int. Cl.
*G06N 3/04*  (2006.01)
*A61B 5/04*  (2006.01)

(52) U.S. Cl.
CPC ....... *G06N 3/0445* (2013.01); *A61B 5/04001* (2013.01)

(58) Field of Classification Search
CPC .......... G06N 3/04; G06N 3/0445; G06N 3/08; A61B 5/04001; G05B 13/027;
(Continued)

(56) References Cited

U.S. PATENT DOCUMENTS

| | | | |
|---|---|---|---|
| 2004/0267320 A1* | 12/2004 | Taylor .................. | A61F 2/72 607/2 |
| 2010/0274746 A1* | 10/2010 | Rickert .............. | G06K 9/00536 706/14 |

(Continued)

OTHER PUBLICATIONS

Sussillo et al., "Making brain-machine interfaces robust to future neural variability", Nature Communications, Published Dec. 13, 2016. (Date precludes usage).*

(Continued)

*Primary Examiner* — Dave Misir
(74) *Attorney, Agent, or Firm* — Lumen Patent Firm (57) ABSTRACT

A brain machine interface (BMI) to control a device is provided. The BMI has a neural decoder, which is a neural to kinematic mapping function with neural signals as input to the neural decoder and kinematics to control the device as output of the neural decoder. The neural decoder is based on a continuous-time multiplicative recurrent neural network, which has been trained as a neural to kinematic mapping function. An advantage of the invention is the robustness of the decoder to perturbations in the neural data; its performance degrades less—or not at all in some circumstances—in comparison to the current state decoders. These perturbations make the current use of BMI in a clinical setting extremely challenging. This invention helps to ameliorate this problem. The robustness of the neural decoder does not come at the cost of some performance, in fact an improvement in performance is observed.

5 Claims, 6 Drawing Sheets

(58) Field of Classification Search
CPC .......... G05B 2219/33025; G05B 2219/33027; G05B 2219/23067
USPC .......................................................... 706/23
See application file for complete search history.

(56) References Cited

U.S. PATENT DOCUMENTS

2011/0224572 A1* 9/2011 Gilja .................... A61F 2/72
                                                    600/545
2013/0311412 A1* 11/2013 Lazar .................... H03M 1/82
                                                    706/16

OTHER PUBLICATIONS

Sussillo et al., "A recurrent neural network for closed-loop intracortical brain-machine interface decoders", Journal of Neural Engineering, Published Mar. 19, 2012.*

Sutskever, Ilya et al. Generating text with recurrent neural networks. Proceedings of the 28th International Conference on Machine Learning (ICML-11). 2011.

Sussillo, David, et al. A recurrent neural network for closed-loop intracortical brain-machine interface decoders. Journal of neural engineering 9.2 (2012): 026027.

Cunningham et al. A closed-loop human simulator for investigating the role of feedback control in brain-machine interfaces. Journal of neurophysiology, 105(4):1932-1949, Apr. 2011.

Chestek et al. Long-term stability of neural prosthetic control signals from silicon cortical arrays in rhesus macaque motor cortex. Journal of neural engineering, 8(4):045005, Jul. 2011.

Santhanam et al. A high-performance brain-computer interface. Nature, 442(7099):195-198, Jul. 2006.

Ryu. Human cortical prostheses: lost in translation? Neurosurgical Focus, 2009.

Churchland et al. Tech-niques for extracting single-trial activity patterns from large-scale neural recordings. Current opinion in neurobiology, 17(5):609-618, Oct. 2007.

Kim et al. Neural control of computer cursor velocity by decoding motor cortical spiking activity in humans with tetraplegia. Journal of neural engineering, 5(4):455-476, Dec. 2008.

* cited by examiner

MULTIPLICATIVE RECURRENT NEURAL NETWORK FOR FAST AND ROBUST INTRACORTICAL BRAIN MACHINE INTERFACE DECODERS

CROSS-REFERENCE TO RELATED APPLICATIONS

This application claims priority from U.S. Provisional Patent Application 62/037,441 filed Aug. 14, 2014, which is incorporated herein by reference.

STATEMENT OF GOVERNMENT SPONSORED SUPPORT

This invention was made with Government support under contracts 8DP1HD075623-04, R01NS076460 awarded by the National Institutes of Health, and under contract N66001-10-C-2010 awarded by the Defense Advanced Research Projects Agency. The Government has certain rights in the invention.

FIELD OF THE INVENTION

This invention relates to decoders for brain machine interfaces.

BACKGROUND OF THE INVENTION

Brain-machine interface (BMI) systems convert neural signals from motor regions of the brain into control signals to guide prosthetic devices. The ultimate goal of BMIs is to improve the quality of life for people with paralysis by providing direct neural control of prosthetic arms or computer cursors. While considerable research over the past 15 years has led to compelling BMI demonstrations, there remain several challenges to achieving clinically viable BMI systems. In this invention, we focus on the challenge of increasing BMI performance and robustness.

SUMMARY OF THE INVENTION

The present invention provides a brain machine interface (BMI) to control a device. The BMI has a neural decoder, which is a neural to kinematic mapping function with neural signals as the input to the neural decoder and kinematics to control the device as the output of the neural decoder. The neural decoder is based on a continuous-time multiplicative recurrent neural network, which has been trained as a neural to kinematic mapping function. The device to be controlled could be a robotic arm, a prosthetic device or a cursor on a computer screen.

In one embodiment, the outputted kinematics could be normalized position over time and velocity over time.

In another embodiment, the neural training data used for training of the neural to kinematic mapping function has been modified. The neural training data could, for example, be modified by randomly adding and removing spikes such that the mean number of spikes is preserved on average.

In yet another embodiment, the neural decoder could have been trained with neural and kinematic data sets collected over multiple days.

In yet another embodiment, the neural decoder could have been trained with neural and kinematic data sets collected over five or more days.

Embodiments of the invention offer the following advantages:

1. State of the art robustness to variations and perturbations in the day-to-day and moment-to-moment neural data. This robustness may help to enable the clinical use of BMIs.
2. State of the art performance of the neural decoder.
3. The ability to improve the decoder by using data from previous days, something the previous decoders were unable to do.

BRIEF DESCRIPTION OF THE DRAWINGS

FIG. 1 shows a schematic of the experimental setup and MRNN (Multiplicative Recurrent Neural Network) decoder. A monkey performed a target acquisition task using his hand while multiunit spikes were recorded from two multi-electrode arrays in motor cortex. Data from many days (e.g. 2 or more days, preferably 5 or more days) of this task were used to train two parallel MRNNs such that velocity and position could be read out from the state of their respective internal dynamics. These internal dynamics are a function of the binned spike counts; thus, the MRNN architecture can conceptually be thought of as selecting which internal dynamics rules are active at any given time based on the spike count inputs. During closed-loop use, the decoded velocity and position commands from the parallel networks were blended together to continuously update the cursor position displayed back to the monkey.

FIGS. 2A-B FIG. 2A shows between-day variability of the structure of neural activity recorded during center-out reaching over the course of many months. The shading at the intersection of row i and column j, corresponds to how differently the observed neural activity covaried during recording sessions i and j. Specifically, we have plotted the minimum subspace angle between subspaces spanned by the top 10 eigenvectors of each day's mean-activity-subtracted covariance matrix. These 10 eigenvectors captured on average 51 (46)% of single-trial variance for monkeys R (L).

FIGS. 3A-C show an example of high performance closed-loop BMI control using the MRNN Decoder. Cursor trajectories from eight representative and consecutive center-out-and-back trials of a Radial 8 Task in which the subject had to move a cursor over a target which alternated between the center of the workspace and one of the peripheral locations. The cursor was either controlled by the monkey's hand position (FIG. 3A), the MRNN decoder (FIG. 3B), or the FIT-KF decoder trained from the same day's training data (FIG. 3C). The FIT-KF decoder is the existing state of the art for BMI decoding algorithms. The bounding boxes show the target acquisition area, and the order of target presentation is denoted with green numbers. Dataset R.2014.04.03.

FIGS. 4A-B show for two monkeys that the MRNN is robust to a natural sampling of neural variability despite trained without access to the most recent several months of data. Each circle corresponds to the mean closed-loop BMI performance using MRNN (medium grey), FIT-long (dark grey), and FIT-old (light grey) decoders when evaluated on six different experiment days. The labeled rectangles denote the time periods from which training data for each decoder came from. The triplet of decoders with the more recent available training day was evaluated on the first three experiment days, and the triplet with less (and more distant) training data was evaluated on the last three experiment days. For both monkeys, only the MRNN decoder consistently was able to perform the task. To aid the interpretation of these historical decoder performances, the dotted lines show the average performance across the experiment days using the native arm (410) or a FIT decoder trained from that same day's arm reaches (420).

FIGS. 5A-B shows that the MRNN is robust to unexpected loss of neural input channels. Closed-loop BMI performance using the MRNN (510) and FIT-KF (520) decoders while simulating an unexpected loss of 0 to 10 channels by setting the firing rates of these channels to zero. The grand mean and SEM of performance is shown for each decoder as a function of how many channels were removed. Stars denote conditions for which the MRNN significantly outperformed FIT-KF across sessions (p<0.05, paired t-test). The fractions above each condition specify for how many of the individual evaluation days each decoder performed significantly better according to success rate and time to target. Channel-dropping order was determined by the mutual information between that channel's spike count and target direction during arm-controlled reaches. Top line tick mark numbers above the x-axis are for 510, while the bottom line tick mark number above the x-axis are for 520.

FIGS. 6A-B show that training data spike rate perturbations improve closed-loop MRNN performance. FIG. 6A shows robustness to channel dropping. We evaluated the closed-loop BMI performance of the MRNN decoder trained with (610) and without (620) the training data spike rate perturbation innovation. Both decoders were evaluated on the same days with firing rates on the top 0 to 10 channels set to zero (similar to FIGS. 4A-B). Each circle corresponds to a decoder's mean performance on a given evaluation day. Filled circles denote days where there was a significance performance difference (p<0.05) between the two decoders tested. The line shows the grand mean performance for each decoder. The MRNN trained with perturbed firing rates consistently outperformed the MRNN trained without these training data perturbations when faced with channel-dropped neural input. FIG. 6B shows historical training data experiments. MRNNs were trained without access to recent training data, as in FIG. 3A-C, either with (630) or without (640) training data spike rate perturbations. We trained decoders from both of monkey R's historical training data periods and from monkey L's longer historical training data period. Closed-loop BMI performance using these decoders was then compared on the same evaluation day in alternating blocks. The plot shows the mean time to target for each block. For all three pairs of decoders compared, the MRNN with spike rate perturbations had significantly faster times to target (p<0.05 averaged across all trials). Datasets R.2014.03.21 & L.2014.04.04.

DETAILED DESCRIPTION OF THE INVENTION

Figure 1:
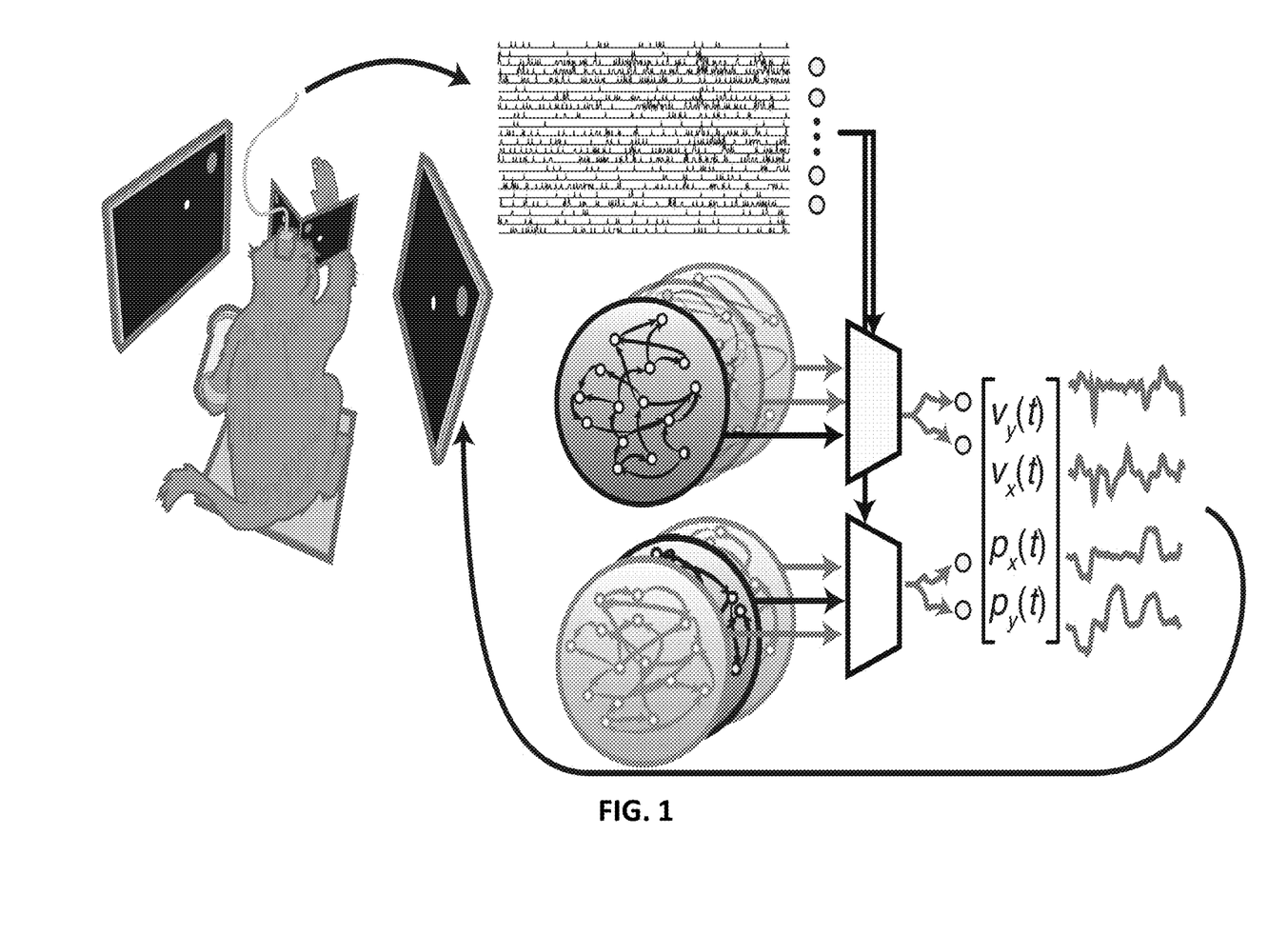
Figure 2A:
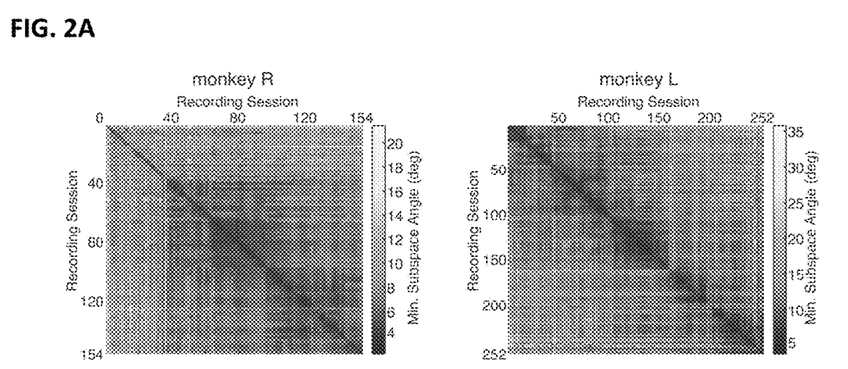
Figure 2B:
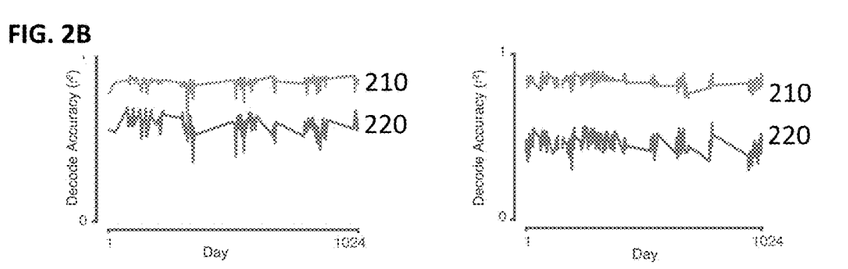
FIG. 2B shows an MRNN (210) and FIT-long (blue) decoder were trained using data from all of the recording sessions in FIG. 2A. The plots show the decoding accuracy of each decoder when decoding hand velocity from held-out trials from each of these days. Note that the horizontal axis now shows chronological days instead of consecutive recording session number as in FIG. 2A.
Figure 3A:
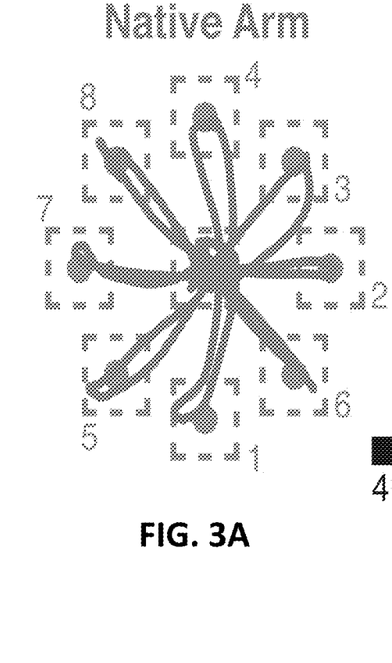
Figure 3B:
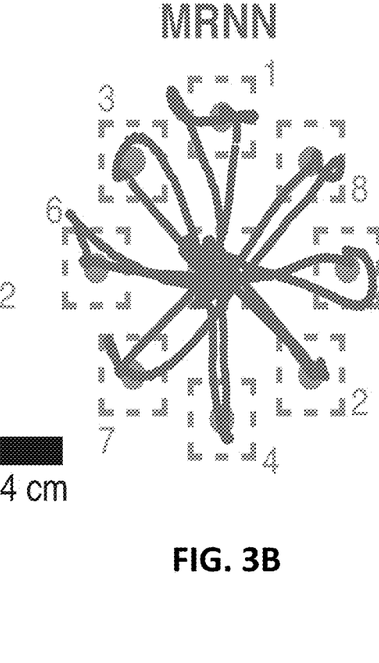
Figure 3C:
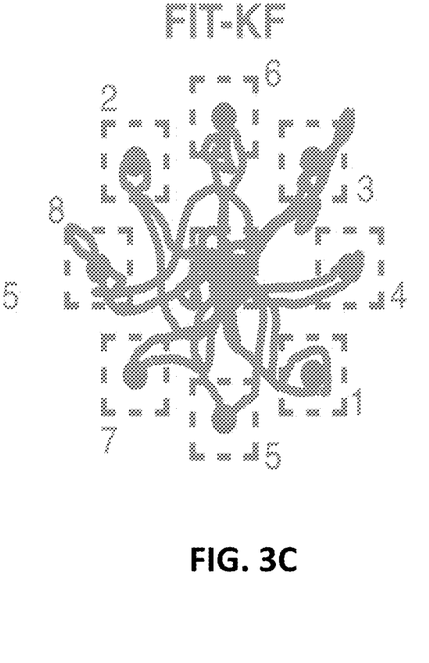
Figure 4A:
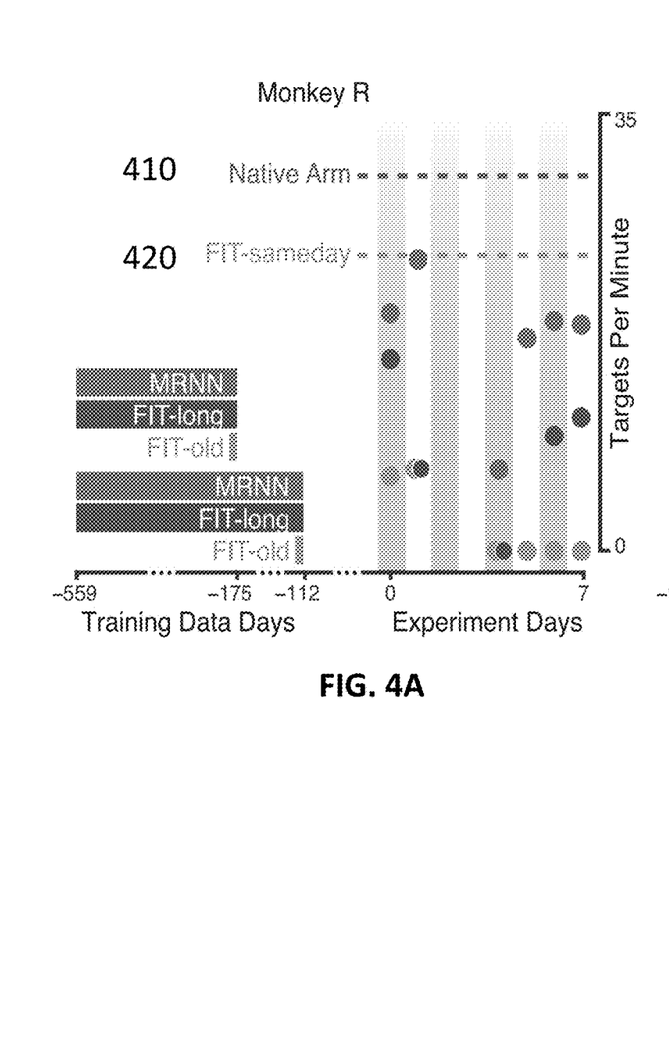
Figure 4B:
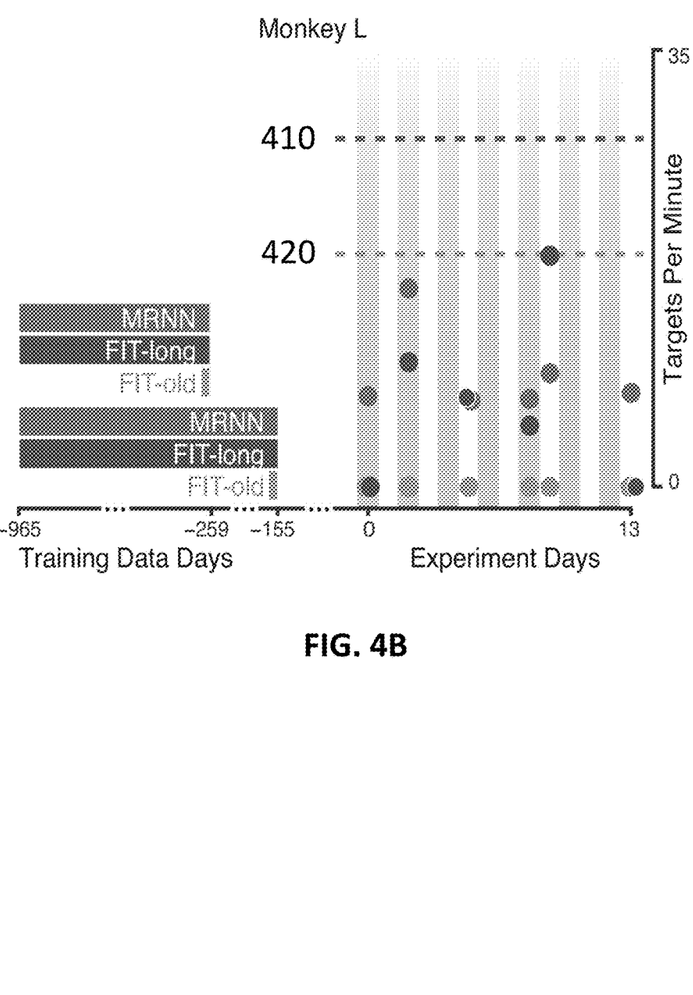
Figure 5A:
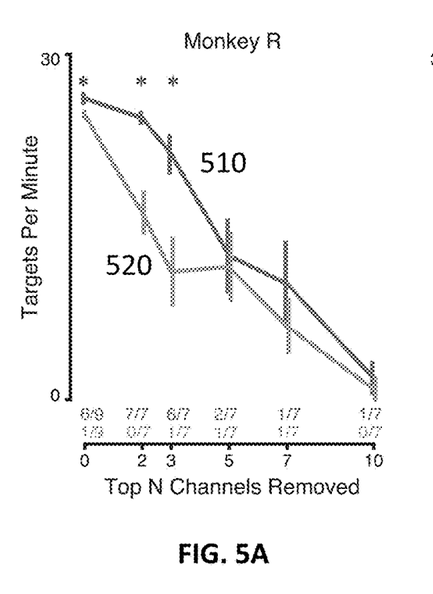
Figure 5B:
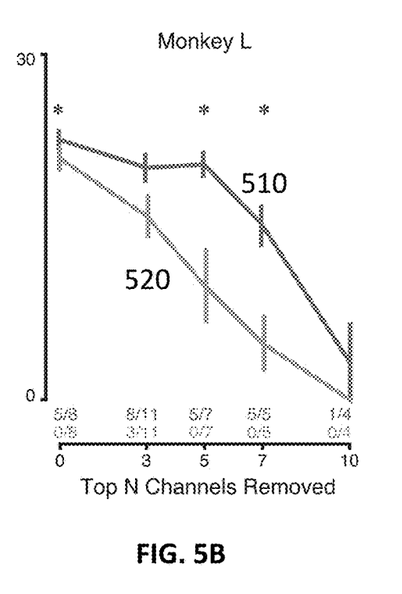
Figure 6A:
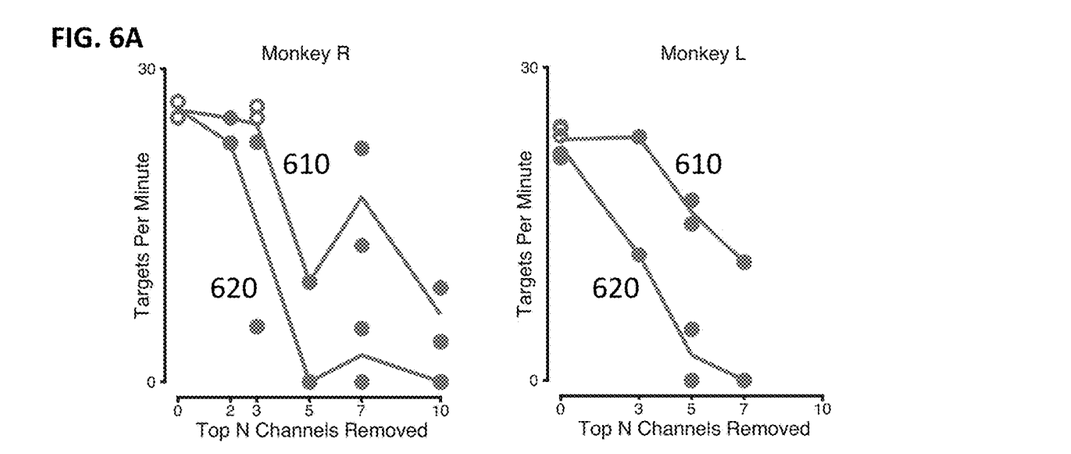
Figure 6B:
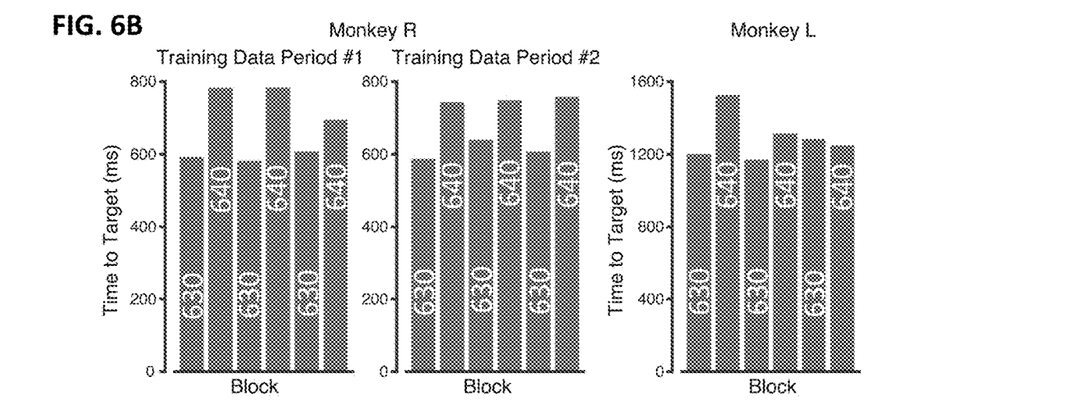

The present invention also referred to as Big-Data Multiplicative Recurrent Neural Network (BD-MRNN) is a supervised neural network and training method for incorporating and modifying multiple previous days training datasets (historical data) to improve both raw performance and robustness in the daily operation of brain-machine interface (BMI) decoders.

MRNN Definition

The generic recurrent network model is defined by an N-dimensional vector of activation variables, x, and a vector of corresponding "firing rates", r=tan h(x). Both x and r are continuous in time and take continuous values. In a standard RNN model, the input affects the dynamics as an additive time-dependent bias in each dimension. In the MRNN model, the input instead directly parameterizes the weight matrix, allowing for multiplicative interactions between the input and the hidden state. One view of this multiplicative interation is that the hidden state of the recurrent network is selecting an appropriate decoder for the statistics of the current dataset. The equation governing the dynamics of the activation vector is of the form suggested in Suskever 2011, but adapted for this invention to continuous time $$\tau \dot{x}(t) = -x(t) + J^{u(t)} r(t) + b^x. \quad (0.1)$$

The N×N×F tensor $J^{u(t)}$ defines the values of the recurrent connections of the network, which are dependent on the I-dimensional input, u(t). In the MRNN, $J^{u(t)}$ is factorized such that the input is linearly combined into F factors. Specifically, $J^{u(t)}$ is factorized according to $$J^{u(t)} = J^{xf} \cdot diag(J^{fu} u(t)) \cdot J^{fx}, \quad (0.2)$$

where $J^{xf}$ has dimension N×F, $J^{fu}$ has dimension F×I, $J^{fx}$ has dimension F×N, and diag(v) takes a vector, v, and returns a diagonal matrix with v along the diagonal. One directly controls the complexity of interactions by choosing the number of factors, F. If F=N², we recover a full N×N×N tensor. If F=1, $J^{u(t)}$ is a rank-one matrix whose singular value is function of u(t).

Finally, the network has a constant bias, $b^x$, and the neuronal time constant, τ, sets the time scale of the network.

MRNN Output Definition

The output of the network is a weighted sum of the network firing rates plus a bias, defined by $$z(t) = W_O^T r(t) + b^z, \quad (0.3)$$

where $W_O$ is an N×M matrix and $b^z$ is an M-dimensional bias.

Network Construction for Cursor BMI Decoder

The network equations defined above are used according to the following procedures and parameters in order to build the BD-MRNN BMI decoder.

MRNN Initialization

For our online experiments, the size of the networks are set to N=100 and N=50 with F=N in both cases (see Table 1). One subject uses a single multi-unit electrode arrays (I=96), while the second uses two (I=192). The non-zero elements of the non-sparse matrices $J^{xf}$, $J^{fu}$, $J^{fx}$ are drawn independently from a Gaussian distribution with zero mean and variance $g_{xf}/F$, $g_{fu}/I$, and $g_{fx}/N$ with $g_{xf}$, $g_{fu}$, and $g_{fx}$ defined in Table 1 for the specific BMI task. The elements of $W_O$ are initialized to zero, and the bias vectors $b^x$ and $b^z$ are also initialized to 0.

Concatenating Neural Trials for Seeding the MRNN During Training

The input u(t), to the MRNN, is the vector of binned spikes measured from neural data (see, for example, Sus sillo 2012 for details on standard preprocessing of neural signals, see Δt in Table 1 for bin sizes). By input to the MRNN, we mean in the sense of equation 0.1. This results in a data matrix, $U^j$, of binned spikes of size I×$T^j$ for each actual trial, where $T^j$ is the number of time steps for the $j^{th}$ trial. Five actual trials are then concatenated together to make one "training" trial. The first two actual trials in a training trial are used for seeding the hidden state of the MRNN, and are not used for learning, whereas the final 3 actual trials in the training trial are used for learning. In this way, excepting the first two actual trials in the day's dataset, the entire set of actual trials are used for learning, by incrementing the actual trial index that begins a training trial.

Perturbing the Neural Input During Training

A key element of training robustness to nonstationarities in the neural code is the introduction of perturbations to the neural spike trains that are used to train the MRNN. The concatenated input in a given training trial, $\hat{U}=[U^i, \ldots, U^{i+4}]$ are perturbed by adding and removing spikes from each channel. We focus on channel c of the $j^{th}$ training trial, i.e., a row vector of data, $\hat{U}_{c,:}^j$. Let the number of spikes in $\hat{U}_{c,:}^j$ be $n_c^j$ before perturbation. This number is perturbed according to $$\hat{n}_c^j = \eta^j \eta_c n_c^j, \quad (0.4)$$

where both $\eta^j$ and $\eta_c$ are Gaussian variables with a mean of one and standard deviations of $\sigma_{trial}$ and $\sigma_{channel}$, respectively (see Table 1). Conceptually, $\eta^j$ models a global modulation in the array across all channels (e.g. changes in subject arousal), while $\eta_c$ models channel by channel perturbations, such as uncontrolled channel dropping or moving baselines in individual neurons. If $\hat{n}_c^j$ is less than zero or greater than $2n_c^j$, it is resampled according to equation 0.4, which keeps the average number of perturbed spikes in a given channel and training trial the same as the average number of unperturbed spikes in the same channel and training trial. Otherwise, if $\hat{n}_c^j$ is greater than $n_c^j$, then $\hat{n}_c^j - n_c^j$ spikes are added to random time bins of the training trial. If $\hat{n}_c^j$ is less than $n_c^j$, then $n_c^j - \hat{n}_c^j$ spikes are randomly removed from time bins of the training trial that already had spikes. Finally, if $\hat{n}_c^j = n_c^j$, nothing is changed.

The process of perturbing the binned spiking data occurs on every iteration of the optimization algorithm. For example, in a batch gradient descent algorithm, the perturbation described by equation 0.4 happens after each update of the network parameters.

Using Many Days Training Data

The typical methodology for training a closed-loop BMI decoder involves training on a session-by-session basis. This means that every day, the subject engages in a control task, for which both input (neural) and supervisory (kinematics) signals are collected. After this session-by-session training period, a BMI is optimized to perfrom well on this data exclusively.

The second critical component to acheiving both performance and robustness in the BD-MRNN decoder is using many days of training data. In our laboratory experiments, we use multiple years of training data (see Table 1). Because of the extreme nonstationarities of the neural data, this aspect of the BD-MRNN training methodology is unintuitive. The nonlinear, multiplicative architecture of the MRNN utilizes the regularities that across many days do exist in a dataset comprising many days. In comparison, the (due to BD-MRNN, no longer) state-of-the-art linear Kalman Filter methods, including previous days data would result in potentially very poor decoders.

Network Output

We train two MRNN networks to each output a 2-dimensional signal. One network is trained to output the normalized position through time in both the horizontal (x) and vertical (y) spatial dimensions. The other MRNN is trained to output the velocity through time, also in the x and y dimensions. We calculate the hand velocities from the positions numerically using central differences.

Since the MRNN decoder outputs both normalized position and velocity, we combine both for our final decoded position signal. The decode used during BMI mode, $d_x(t)$, $d_y(t)$ is a mix of both velocity and position, defined by $$d_x(t) = \beta(d_x(t-\Delta t) + \gamma_v v_x(t-\Delta t)\Delta t) + (1-\beta)\gamma_p p_x(t) \quad (0.5)$$

$$d_y(t) = \beta(d_y(t-\Delta t) + \gamma_v v_y(t-\Delta t)\Delta t) + (1-\beta)\gamma_p p_y(t) \quad (0.6)$$

where $v_x$, $v_y$, $p_x$, $p_y$ are the normalized velocity and positions in the x and y dimensions and $\gamma_v$, $\gamma_p$ are factors that convert from the normalized velocity and position, respectively, to the physical values associated with the workspace. The parameter $\beta$ sets the amount of velocity vs. position decoding (see Table 1).

Training and Running the Networks

A network is simulated by integrating equation 0.1 using the Euler method at a time step of $\Delta t = \tau/5$ and then evaluating equation 0.3.

The parameters of the network are trained offline to reduce the averaged squared error between the measured kinematic training data and the output of the network, $z(t)$. Specifically, we use the Hessian-Free (HF) optimization method for RNNs (but adapted to the continuous-time MRNN architecture). HF is an exact $2^{nd}$ order method that uses back-propagation-through-time to compute the gradient of the error with respect to the network parameters. The set of trained parameters is $\{J^{xf}, J^{fu}, J^{fx}, b^x, b^z\}$. The HF algorithm has some critical parameters, such as the mini-batch size, the initial lambda setting, and the max number of CG iterations. We set these parameters to $\frac{1}{5}$ times the total number of trials, 0.1, and 50, respectively.

After training, the networks are copied into the embedded real-time environment (xPC), and run in closed-loop, to operate online in BMI mode. Specifically, at each time point the RNN module receives binned spikes and outputs the current estimate of the hand position, which is used to display the cursor position on the screen. During BMI mode the neural spikes are not perturbed in any way. The values $v_x(0)$ and $v_y(0)$ are initialized to 0, as is the MRNN hidden state.

Model Parameters

The parameters of the model of an exemplary embodiment are listed in Table 1.

TABLE 1

Values for network and training parameters for Monkeys R and L, as described in the invention report.

|  | Monkey R | Monkey L |
| --- | --- | --- |
| $\Delta t$ | 20 ms | 30 ms |
| $\tau$ | 100 ms | 150 ms |
| N | 100 | 50 |
| F | 100 | 50 |
| $\sigma_{trial}$ | 0.045 | 0.045 |
| $\sigma_{channel}$ | 0.3 | 0.3 |
| $g_{xf}$ | 1.0 | 1.0 |
| $g_{fu}$ | 1.0 | 1.0 |
| $g_{fx}$ | 1.0 | 1.0 |
| I | 192 | 96 |
| # years training data | 0.25 to 3 | 0.25 to 3 |
| $\beta$ | 0.99 | 0.99 |

Remark on the Use of Multiple Days of Training Data

One critical aspect of the invention is using multiple days of training data. At first glance, it may seem straightforward that more data should always improve the quality of performance on some supervised system, such as a neural network. However, this is only true under a very specific and very commonly met assumption. This assumption is *not* met in the BMI setting. The assumption is that the data used to optimize ("train") the neural network comes from the same distribution as the data used in the network during operation (during so-called "validation" or "testing"). When this assumption is met, indeed more training data leads to a better neural network that performs better on generalization testing. To reiterate, this assumption is *not* met in the neural data used to train BMIs.

As an example analogous to the BMI setting, imagine that we are interested in building a neural network to classify hand written letters from different users. Specifically, we want to classify different users based on how they write the letter 'h' (e.g. user 1 wrote these 'h' letters, while user 2 wrote those 'h' letters.) If our dataset contained only handwritten 'h' letters, then adding more and more 'h' letters would definitely improve our classification of user 1 from user 2, as per common understanding. However, imagine that we had access to other letters that the users wrote, such as 'n', and 'x'. If our job is only to classify different users based on the letter 'h', then it appears that including 'x' as training data to an 'h' classifier could only hurt the it's performance on classifying the letter 'h'.

However, you could also reason that if you included 'n' in your 'h' classifier, perhaps one could still improve the classifier because the letter 'n' shares some common features with the letter 'h'. It's not at all clear what would happen if we threw in the letters from 'a' to 'z'. We can summarize that adding more training data (letters different from 'h'), when the data does not come from the test distribution ('h' letters), will not obviously help improve the network's performance.

The previous example is analogous to current situation in BMI research. We would like to classify different user intentions, such as moving a computer cursor up or down (analogous to classifying user 1 or user 2) based on neural data (the letters). However, each day the neural data upon which we classify changes dramatically (some days we have 'h' letters to classify user 1 vs user 2, some days we have 'x' letters). Further, the changes in neural data are not under our control. So we never know whether we are going to be looking at an 'h' or an 'x' or a 'n'. If it's an 'h' day, than using a previous 'x' day seems like a bad idea.

It is a fact, in the BMI setting, the neural data collected using modern devices (e.g., Utah multi electrode array) varies dramatically from day-to-day, even when the subject is requested to perform the exact same task, and the experimental conditions are reproduced to as exacting conditions as the experimental environment will allow. It is unclear why the neural data varies so dramatically, although many believe it is a combination of the underlying complexities of the neural code, combined with the inevitable limitations of reading biological electrical signals with limited silicon-based hardware.

The variation in neural signals has led to the widely held view in the BMI field that using data from multiple days is in fact quite problematic. As a result, the standard—and state of the art—practice is to record training data each and every day, and perhaps more than once a day. This training data is then used to run a BMI decoder for some amount of time on that same day. Anecdotally, many researchers have tried to incorporate more data than just a single day, though it is widely held as a bad idea because it often fails to improve things. Sometimes using yesterday's data as well as today's data improves things, sometimes it does not. Surely using data from over 1 month ago is a bad idea to include in a training set for today's BMI decoder.

These widely held views about which data to use for training a closed-loop BMI decoder are based primarily on using a linear decoding method, the Kalman filter. As a linear method, the Kalman filter can only give an average response to many days of training data, so if neural data from one month ago is indeed different from today's neural data, indeed the Kalman filter trained using the old data will result in a very poor decoder on new data from today. Thus the vast majority of experts (likely all) in the field would consider it non-straightfoward to devise a method whereby previous data from three to six months ago, as we have shown empirically, is helping to decode today's neural data.

For our invention, we made a systematic study of how one day's neural data compares to another day's. We did this using an analysis technique called the principal subspace angle. The scientific result of this analysis is that some days are more similar to others, while some days are very different. Further, similar neural data tends to come in blocks of time, but oddly, data from many months ago can be quite similar to today's neural data (the exact similarity structure is beyond the scope of this introduction). Naturally, it would be desirable to use only training data from days that are similar to the day on which you were interested in running the decoder (use 'n's and not 'x's to help classify the users 1 and 2 based on how they write the letter 'h'). However, it is very hard to know, a priori, which days will help.

To sidestep this problem, we used a highly nonlinear decoder, a multiplicative recurrent neural network (MRNN). The MRNN is powerful enough to handle the varying neural data from many days, even when the neural data is significantly different from day to day. So long as there are some similarities in the neural data between days (e.g. a 'n' similar to an 'h'), the MRNN is smart enough to use this data to improve the BMI decode. If the training data bears little similarity to today's neural data ('x' letters are not similar to 'h' letters), the MRNN is smart enough to ignore it while decoding today's neural data.

Embodiments of the invention could be envisioned as a brain machine interface controlling a device such as a robotic arm, a prosthetic device or a cursor on a computer screen. The brain machine interface receives neural signals from a subject's brain, which are processed by one or more neural decoders. The neural decoders are either functionalized with method steps to execute the signal processing steps and/or are hardware systems for processing the neural signals as described herein. The neural decoders could include computer hardware and software devices/technology for its operation(s). The neural decoders are interfaced with the device to control the kinematics of the device based on the processed neural signals.

REFERENCES

John P Cunningham et al. A closed-loop human simulator for investigating the role of feedback control in brain-machine interfaces. Journal of neurophysiology, 105(4): 1932-1949, April 2011.
Cynthia A Chestek et al. Long-term stability of neural prosthetic control signals from silicon cortical arrays in rhesus macaque motor cortex. Journal of neural engineering, 8(4):045005, July 2011.
Gopal Santhanam et al. A high-performance brain-computer interface. Nature, 442(7099):195-198, July 2006.
S I Ryu. Human cortical prostheses: lost in translation? Neurosurgical Focus, 2009.
Mark M Churchland et al. Techniques for extracting single-trial activity patterns from large-scale neural recordings. Current opinion in neurobiology, 17(5):609-618, October 2007.

Kim et al. Neural control of computer cursor velocity by decoding motor cortical spiking activity in humans with tetraplegia. Journal of neural engineering, 5(4):455-476, December 2008.

Sutskever, Ilya et al. Generating text with recurrent neural networks. Proceedings of the 28th International Conference on Machine Learning (ICML-11). 2011.

Sussillo, David, et al. A recurrent neural network for closed-loop intracortical brain—machine interface decoders. Journal of neural engineering 9.2 (2012): 026027.

What is claimed is:

1. A brain machine interface to control a device, comprising: the brain machine interface having a neural decoder wherein the neural decoder is a continuous-time multiplicative recurrent neural network trained as a neural to kinematic mapping function with neural signals from a brain of a subject as input to the neural decoder and kinematics to control the device as output of the neural decoder, wherein neural training data used for training the neural to kinematic mapping function has been modified by randomly adding and removing spikes such that the mean number of spikes is preserved on average, and wherein the brain machine interface converts the neural signals from motor regions of the brain of the subject into kinematic control signals to control the device.

2. The brain machine interface as set forth in claim 1, wherein the outputted kinematics is normalized position over time and/or velocity over time.

3. The brain machine interface as set forth in claim 1, wherein the device to be controlled is a robotic arm, a prosthetic device or a cursor on a computer screen.

4. The brain machine interface as set forth in claim 1, wherein the neural decoder has been trained with neural and kinematic data sets collected over multiple days.

5. The brain machine interface as set forth in claim 1, wherein the neural decoder has been trained with neural and kinematic data sets collected over five or more days.

* * * * *